US009872651B2

(12) United States Patent
Berke

(10) Patent No.: US 9,872,651 B2
(45) Date of Patent: Jan. 23, 2018

(54) MEDICAL WORKSTATION

(75) Inventor: Ralph Berke, Gessertshausen (DE)

(73) Assignee: KUKA Roboter GmbH, Augsburg (DE)

( * ) Notice: Subject to any disclaimer, the term of this patent is extended or adjusted under 35 U.S.C. 154(b) by 409 days.

(21) Appl. No.: 13/419,716

(22) Filed: Mar. 14, 2012

(65) Prior Publication Data

US 2012/0265071 A1  Oct. 18, 2012

(30) Foreign Application Priority Data

Mar. 22, 2011  (DE) ................. 10 2011 005 917

(51) Int. Cl.
| | |
|---|---|
| *A61B 8/00* | (2006.01) |
| *A61B 5/00* | (2006.01) |
| *A61B 1/00* | (2006.01) |
| *A61B 5/06* | (2006.01) |
| *A61B 34/32* | (2016.01) |
| *A61B 34/30* | (2016.01) |
| *A61B 34/00* | (2016.01) |

(Continued)

(52) U.S. Cl.
CPC .......... *A61B 5/704* (2013.01); *A61B 1/00149* (2013.01); *A61B 5/066* (2013.01); *A61B 34/30* (2016.02); *A61B 34/32* (2016.02); *A61B 34/76* (2016.02); *A61B 34/20* (2016.02); *A61B 2017/00119* (2013.01); *A61B 2090/378* (2016.02)

(58) Field of Classification Search
USPC ....................................... 600/439
See application file for complete search history.

(56) References Cited

U.S. PATENT DOCUMENTS 4,979,949 A * 12/1990 Matsen et al. ................. 606/53
6,459,926 B1 * 10/2002 Nowlin et al. ............... 600/429

(Continued)

FOREIGN PATENT DOCUMENTS

| WO | 2005/039391 A2 | 5/2005 |
| WO | 2009/045827 A2 | 4/2009 |

(Continued)

OTHER PUBLICATIONS

German Patent Office; Office Action in German Patent Application No. 10 2011 005 917.2 dated Feb. 8, 2012; 5 pages.

(Continued)

*Primary Examiner* — Amelie R Gillman
(74) *Attorney, Agent, or Firm* — Wood Herron & Evans LLP

(57) ABSTRACT

The invention relates to a medical work station which has a medical instrument which is intended to be inserted at least partially into the interior of a lying being for treating the latter, an imaging device which is set up to create image data records of the interior of the living being during the treatment, and a robot. The robot includes a robot arm having a plurality of members situated one after another, on which the imaging device or the medical instrument may be situated, and a control device intended for moving the robot arm, which is set up to move the robot arm in such a way that the imaging device attached to the robot arm follows a motion of the medical instrument, or the medical instrument attached to the robot arm follows a motion of the imaging device.

12 Claims, 3 Drawing Sheets

Figure 1:
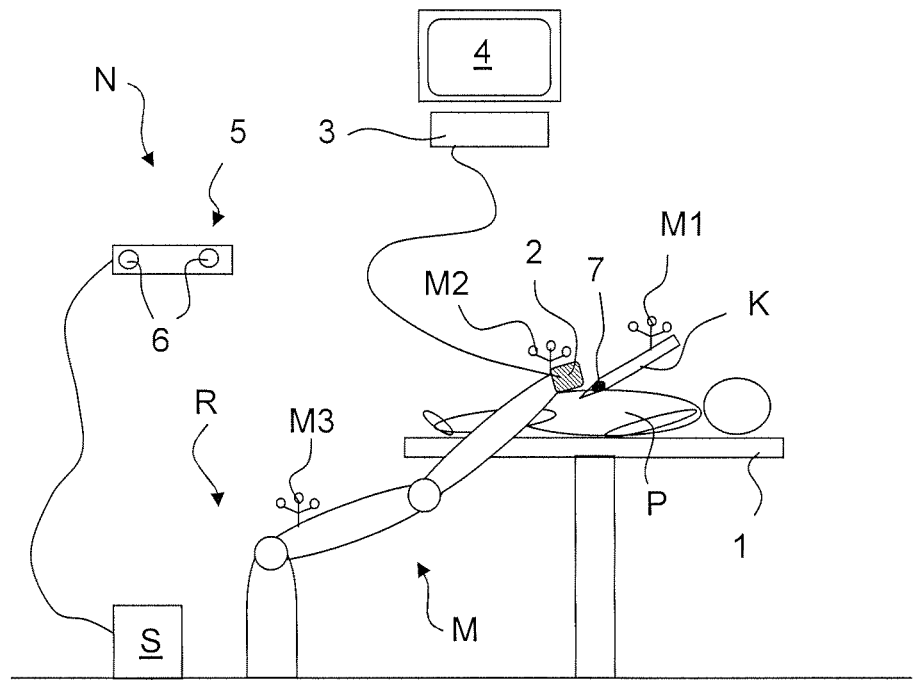

(51) Int. Cl.
    *A61B 17/00*        (2006.01)
    *A61B 34/20*        (2016.01)
    *A61B 90/00*        (2016.01)

(56) References Cited

U.S. PATENT DOCUMENTS

| | | |
|---|---|---|
| 6,626,832 B1 | 9/2003 | Paltieli et al. |
| 2002/0120188 A1 | 8/2002 | Brock et al. |
| 2004/0128026 A1* | 7/2004 | Harris et al. ............... 700/245 |
| 2005/0033161 A1 | 2/2005 | Birkenbach et al. |
| 2005/0107808 A1 | 5/2005 | Evans et al. |
| 2007/0142823 A1* | 6/2007 | Prisco et al. ................ 606/1 |
| 2008/0247506 A1* | 10/2008 | Maschke ..................... 378/15 |
| 2009/0082784 A1* | 3/2009 | Meissner et al. ............ 606/130 |
| 2009/0088897 A1* | 4/2009 | Zhao et al. .................. 700/250 |
| 2009/0227910 A1* | 9/2009 | Pedersen et al. ............. 601/2 |
| 2010/0137880 A1* | 6/2010 | Nahum et al. ............... 606/130 |
| 2011/0069818 A1* | 3/2011 | Muller ........................ 378/197 |
| 2011/0190790 A1* | 8/2011 | Summerer et al. .......... 606/130 |

FOREIGN PATENT DOCUMENTS

| | | |
|---|---|---|
| WO | 2009/045885 A2 | 4/2009 |
| WO | WO2009121822 * | 10/2009 |
| WO | WO2010017919 * | 2/2010 |

OTHER PUBLICATIONS

European Patent Office; Search Report in European Patent Application No. 12159485.7 dated Jun. 6, 2012; 12 pages.

* cited by examiner

MEDICAL WORKSTATION

The invention relates to a medical work station having a robot.

WO 2009/065827 A1 discloses a medical work station having a robot. The robot includes a robot arm and a control device for moving the robot arm. Attached to an attaching device of the robot arm is for example an endoscope, by means of which the living being is to be treated. In order to ascertain the positions and orientations of the living being relative to the robot arm, a navigation system is provided.

The object of the invention is to create an improved medical work station having a robot.

The object of the invention is fulfilled by a medical work station having

- a medical instrument which is intended to be inserted at least partially into the interior of a living being for treating the latter,
- an imaging device which is set up to create image data records of the interior of the living being during the treatment, and
- a robot which has a robot arm having a plurality of members situated one after the other, on which the imaging device or the medical instrument is positionable, and a control device intended for moving the robot arm, which is set up to move the robot arm in such a way that the imaging device attached to the robot arm follows a motion of the medical instrument or the medical instrument attached to the robot arm follows a motion of the imaging device.

The medical work station according to the invention accordingly includes the medical instrument and the imaging device. The medical instrument is intended to be inserted at least partially into the interior of the living being for treating the latter. The medical instrument is for example a cannula, which is set up to suction off fat tissue of the living being.

By means of the imaging device, image records of the interior of the living being can be recorded during the treatment, i.e., while the medical instrument is at least partially inserted into the interior of the living being. The recorded image records can be used for example to display images assigned to the image records by means of a display device.

Now in order to always, or at least now and then, obtain current image records, in particular of the area of the interior of the living being into which the medical instrument is at least partially inserted, the medical work station has the robot which is set up to move the robot arm in such a way that the imaging device attached to the robot arm follows the motion of the medical instrument or the medical instrument attached to the robot arm follows the motion of the imaging device. If a doctor for example introduces the medical instrument manually at least partially into the interior of the living being, the imaging device, moved by the robot arm, follows in particular constantly the motion of the manually guided medical instrument.

Alternatively, it can be provided that if for example the doctor guides the imaging device manually, the robot automatically moves the medical instrument in such a way that the medical instrument automatically follows the motion of the imaging device.

The imaging device is set up for example to create image records assigned to ultrasound images of the interior of the living being. An ultrasound device can be of relatively small design, and can thus possibly be moved relatively simply by means of the robot. Furthermore, an ultrasound device does not produce any health-threatening radiation, as an x-ray device for example does.

According to one embodiment of the medical work station according to the invention, the latter has a navigation system connected to the control device of the robot, which is set up to ascertain the positions and/or locations of the robot arm, the medical instrument and/or the imaging device, on the basis of which the control device moves the robot arm, so that the imaging device attached to the robot arm follows the motion of the medical instrument or the medical instrument attached to the robot arm follows the motion of the imaging device.

Navigation systems are generally known in medical technology, for example from WO 2009/065827 A1. Navigation systems include a detection device, which may have for example an optical detection device, in particular a camera, a laser tracking system, projectors for structured light or linear projectors. The detection device is set up to detect in a generally known way markers or distinctive areas of the surface of the object on the object, in particular on the surface of the object. On the basis of the detection of the markers or distinctive areas, a computing device of the navigation system can determine the positions of the robot arm, the medical instrument and/or the imaging device, and possibly its orientation, in an essentially generally known way. Thus the medical work station according to the invention can be enabled to determine for example the current position and/or location (=position and orientation) for example of the manually guided medical instrument, in order to track the imaging device attached to the robot arm accordingly.

The medical work station according to the invention can have a display device, which is intended to display an image assigned to the image record visually. Thus the person treating the living being can observe in a relatively simple way the medical instrument inserted at least partially into the interior of the living being.

According to one variant of the medical work station according to the invention, the latter is set up to analyze the image record in areas undesired and/or desired for the treatment of the living being with the medical instrument.

It can then be provided in an advantageous way that the medical work station according to the invention is set up to identify desired or undesired depicted areas in the image depicted by means of the display device. The person treating the living being with the medical instrument can thereby better recognize when the medical instrument inserted at least partially into the interior is leaving the desired area, or at least threatens to leave it. The corresponding areas can be identified for example in color.

In order to warn the person treating the living being, if necessary, according to one variant of the medical work station according to the invention the latter can be set up to produce a warning signal on the basis of the analyzed image record, in particular an acoustic warning signal, if the medical instrument is located outside of the desired area or threatens to leave the latter.

In order to warn the person treating the living being, if necessary, according to one variant of the medical work station according to the invention its medical instrument can have a vibration emitter, and the medical work station according to the invention can be set up to activate the vibration emitter on the basis of the analyzed image record if the medical instrument is located outside of the desired area or threatens to leave the latter.

According to another embodiment of the medical work station according to the invention, the latter is set up to stop or prevent a motion of the robot arm provided with the medical instrument on the basis of the analyzed image record, if the medical instrument is located outside of the desired area or threatens to leave the latter. Thus, if the person treating the living being for example moves the imaging device manually, and the robot automatically tracks the medical instrument following the motion of the imaging device, then according to this variant the robot automatically stops the motion of the medical instrument if the latter threatens to enter an area that it is not supposed to enter.

According to another embodiment of the medical work station according to the invention, the latter has an additional robot with a robot arm having a plurality of members situated one after the other, and with an additional control device intended for moving the additional robot arm, where one of the robot arms is intended to move the imaging device, and the other robot arm is intended to move the medical instrument. The two control devices may also be combined into a single control device. By means of this variant of the medical work station according to the invention, a fully automatic operation for example can be performed on the living being, by both robot arms carrying out their motions automatically.

According to one embodiment of the medical work station according to the invention, the two control devices are coupled with each other in such a way that in the event of a motion of one of the robot arms the other robot arm automatically executes a motion in such a way that the medical instrument follows a motion of the imaging device or the imaging device follows a motion of the medical instrument. In order to achieve this, the two control devices may be designed for example as a master-slave system.

According to one embodiment of the medical work station according to the invention, one of the robot arms is manually movable and the other robot arm, guided by its control device, automatically follows the motion of the manually moved robot arm. The robot arm in question may be moved for example by manual guiding, or by means of a hand-held operating device.

If the manually movable robot arm is provided with the medical instrument, according to another embodiment of the medical work station according to the invention the latter can be set up to prevent a motion of the robot arm provided with the medical instrument, or at least to impede it, if the medical instrument is located outside of the desired area or threatens to leave the latter. The desired area or undesired area may be recognized in particular by means of analyzing the image record.

In particular, if the medical work station according to the invention is to be used to suction off fat tissue from the living being, the safety and the quality of the fat suctioning can be increased by the medical work station according to the invention. Using the imaging device, such as ultrasound for example, fat tissue in particular can be depicted relatively well and efficiently. The intended fat layer to be suctioned off can be visualized thereby for example, in order to be able to suction off the relevant fat layer relatively exactly with the medical instrument in the form of a cannula.

Figure 2:
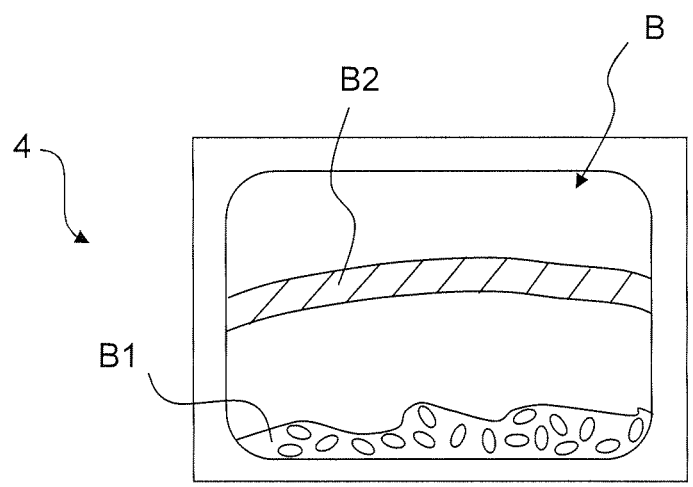
Figure 3:
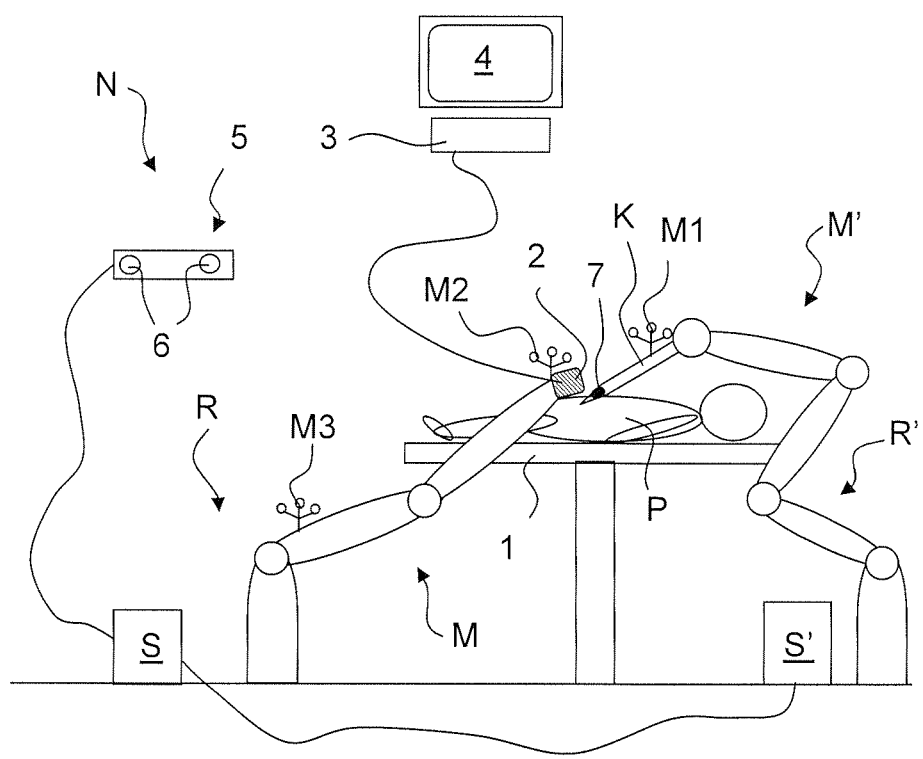
Figure 4:
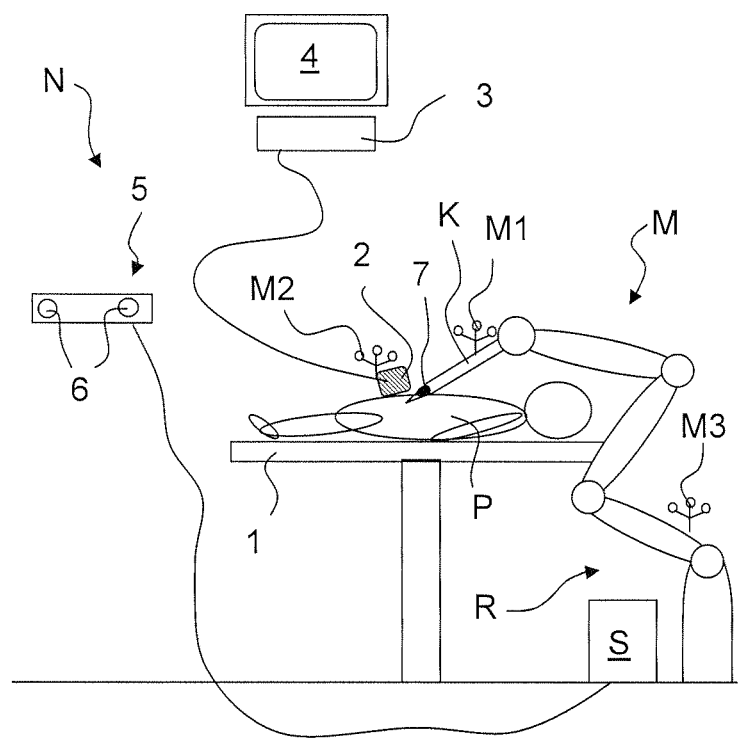

Examples of exemplary embodiments of the invention are depicted in the accompanying schematic drawing. The figures show the following:

FIG. 1 a medical work station having a robot,
FIG. 2 an ultrasound image,
FIG. 3 a medical work station having two robots, and
FIG. 4 another medical work station having a robot.

FIG. 1 shows a medical work station having a patient table 1, on which a living being to be treated, for example a person P, is lying. The medical work station also has a cannula K, by means of which a fat suction is to be performed on the person P. The cannula K is guided manually by a doctor, not shown in greater detail. The cannula K is one example of a medical instrument that can be inserted into the living being.

The medical work station also has a robot R with a robot arm M and a control device S. The robot arm M has a plurality of members following one after the other, which are connected by means of joints and are movable relative to each other in reference to axes. At one end of the robot arm M an ultrasonic transducer 2 is attached or integrated into the robot arm M. The ultrasonic transducer 2 is connected to a computer 3 of the medical work station, and is set up to produce ultrasound images B of the interior of the person P or image records assigned to the ultrasound images B. The ultrasound images B can be depicted by means of a monitor 4 connected to the computer 3. One of the ultrasound images B is depicted in FIG. 2. It shows for example depicted fat tissue B1 and the depicted skin surface B2 of the person P.

The robot arm M has drives, in particular electric drives, which are connected to the control device S. By means of the drives, the robot arm M or its members can be moved relative to each other and controlled by the control device S or by a computer program running on the control device S. In particular, it is thereby possible for the ultrasonic transducer 2 to assume a prescribed position and orientation in space. The drives are regulated as appropriate by the control device S.

In the case of the present exemplary embodiment, the medical work station includes a navigation system N. Navigation systems as such are known to a person skilled in the art for example from WO 2009/065827 A1. Navigation systems may be for example magnetic or optical navigation systems or may be based on RFID, and are employed for example to ascertain the position and possibly the orientation of an object, for example the ultrasound transducer 2, the cannula K or the robot arm M.

In the case of the present exemplary embodiment, the cannula is provided with markers M1, the ultrasonic transducer 2 with markers M2 and the robot arm M with markers M3, by means of which the navigation system N is able to determine the positions or locations, i.e., positions and orientations, of the cannula K, the ultrasonic transducer 2 and the robot arm M in space.

In the case of the present exemplary embodiment, the navigation system N has a detection device 5, which includes for example a stereo camera 6. The stereo camera 6 is set up to take pictures of the markers M1, M2, M3.

The detection device 5 in the case of the present exemplary embodiment is connected to the control device S of the robot R, on which a computer program runs that evaluates in a generally known way the pictures of the markers M1, M2, M3 taken by means of the stereo camera 6, and on the basis of the evaluation determines the positions of the markers M1, M2, M3, and thus the positions of the cannula K, the ultrasonic transducer 2 and the robot arm M in space. This evaluation can also be carried out by the detection device, which then conveys the result of the evaluation to the control device S.

It is thus possible for the control device S, or a computer program running on the control device S, to actuate the drives of the robot arm M in such a way that the latter moves or tracks the ultrasonic transducer 2 in such a way that the ultrasonic transducer 2 and the cannula K maintain a prescribed distance. This makes it possible, during the treatment of the person P by means of the cannula K, for the ultrasonic transducer 2 to produce image records which are assigned to the ultrasound images B in particular of the area of the person P ahead of the cannula K, so that these ultrasound images B are displayed for the doctor operating the cannula K by means of the monitor 4. Accordingly, the ultrasound images B depict online the tissue layer of the person P lying ahead of the cannula K on the monitor 4. The doctor can then decide for example how and where he would like to move the cannula K to suction off the fat tissue. In particular, it can be provided that the control device S always actuates the robot arm M or its drives in such a way that the ultrasonic transducer always follows the individual motion of the cannula K or its syringe. The doctor can thereby be enabled to see on the monitor 4 relatively exactly in which tissue layer of the person P the cannula K is located at the moment.

An image processing program can run on the computer 3, which processes the image records produced by means of the ultrasonic transducer in such a way that fat tissue B1 for example depicted in ultrasound image B is identified for example by color from other areas of the person P. Tissue depicted accordingly can be recognized for example by means of ultrasound elastography. It is also possible for areas of the person P that are not to be treated by means of the cannula K to be depicted with different coloring or marking in ultrasound image B.

Thus it can also be provided that in particular the image processing program running on the computer 3 recognizes when in particular the tip of the cannula K approaches a prohibited area, i.e., an area outside of the fat tissue. It is then possible that the computer 3 produces a signal, on the basis of which the doctor for example is warned acoustically. It is also possible, however, that the cannula K has a vibration emitter, in order to warn the doctor of critical areas when using manual guidance. In this case the computer 3 for example is connected to the cannula K or the vibration emitter.

It is also possible that in particular at the tip of the cannula K a sensor 7 is provided, which is connected in particular to the navigation system N. The sensor 7 can permit for example an improved determination of the position, and possibly the orientation, of the cannula K, in particular its tip. The sensor 7 may be based for example on RFID.

However, the sensor 7 may also be designed so that it recognizes the current tissue type and conveys this information for example to the computer 3. The information may be conveyed for example wirelessly, for example by radio, or else via cable connection. The information coming from the sensor 7 may be used for example for depicting the ultrasound image B.

The medical work station could also be set up so that the operation is documented for example by means of the computer 3, for example for quality assurance.

It is also possible that a preoperative image record of the person P is recorded before the operation. The preoperative image record is in particular a three-dimensional image record, and depicts in particular the area of the operation. The preoperative image record is recorded in particular with a medical device, for example a magnetic resonance device, and during the operation can be merged with or superimposed on the image record recorded by means of the ultrasonic transducer 2, in order to produce a modified image that is displayed instead of the ultrasound image B on the monitor 4.

FIG. 3 shows an additional medical work station. If not described otherwise, then components of the medical work station shown in FIG. 3 which are essentially the same in construction and function as components of the medical work station in FIG. 1 are provided with the same reference labels.

The medical work station shown in FIG. 3 differs essentially from the medical work station shown in FIG. 1 in that it includes a second robot R'. The additional robot R' has an additional robot arm M' and an additional control device S'. The additional robot arm M' includes a number of members following one after the other, which are connected by means of joints and are movable relative to each other in reference to axes. At one end of the additional robot arm M' the cannula K is attached. To that end, the additional robot arm M' includes a suitable attaching device, for example in the form of a flange.

The additional robot arm M' has drives, in particular electric drives, which are connected to the additional control device S'. By means of its drives, the additional robot arm M' or its members can be moved relative to each other, controlled by the additional control device S' or by a computer program running on the additional control device S'. In particular, it is thereby possible for the cannula K to assume a prescribed position and orientation in space. The drives are possibly regulated by the additional control device S'. Thus the cannula K is guided by the additional robot R'.

Thus, in the medical work station of FIG. 3, the robot R guides the ultrasonic transducer 2 and the additional robot R' guides the cannula K. The two robots R, R' or their control devices S, S' are coupled in the case of the present exemplary embodiment into a regulating circuit, so that the robot R' moving the cannula K moves the cannula K only in the permitted fat tissue area. By means of image processing, permitted and non-permitted areas in the ultrasound image B are identified automatically and displayed on the monitor 4. The motion of the additional robot R' can also be limited automatically by means of virtual walls, so that guidance of the cannula K is possible only in the permitted fat tissue area. It is also possible that a common control device, for example the control device S, actuates both robot arms M, M'.

In order to couple the two robots R, R' with each other, their control devices S, S' may be designed as a master-slave system, so that for example for an automated operation the additional control device S' moves the additional robot arm R' in such a way that the cannula K executes a prescribed motion. Because of the coupling of the two control devices S, S', the control device S is enabled to move the robot arm M and hence the ultrasonic transducer 2 in such a way that the latter is at the prescribed distance from the cannula K. In this case, the medical work station of FIG. 3 may be able to get along without the navigation system N.

Instead of the fully automated medical work station of FIG. 3, it can also be provided that two robots R, R' are indeed provided, but during the operation the doctor manually moves one of the two robot arms M, M', preferably the additional robot arm M', to which the cannula K is attached. In particular, it can be provided that the doctor guides the robot arm M, M' in question manually, for example by pulling or pushing on the structure of the corresponding robot arm M, M'. However, it is also possible that he moves the robot arm M, M' in question manually by using a hand-held operating device, not depicted in greater detail but generally known to a person skilled in the art, which is connected to the corresponding control device S, S'.

Because of the coupling of the two control devices S, S', the robot R or its robot arm M moves the ultrasonic transducer 2 at the prescribed distance from the tip of the cannula. In this embodiment, it can then be provided in the case of the present exemplary embodiment that the doctor is no longer able to move the additional robot arm M', or only with the exertion of great effort, as soon as the cannula K advances into a non-permitted area or leaves the fat tissue area. This is detected by the computer 3 by means of image processing, on the basis of the image records recorded by means of the ultrasonic transducer. In this case it may be possible to get along without the navigation system N. It is also possible that the robot arm M, to which the ultrasonic transducer is attached, is moved manually.

FIG. 4 shows an additional medical work station. If not described otherwise, then components of the medical work station shown in FIG. 4 which are essentially the same in construction and function as components of the medical work station in FIG. 1 are provided with the same reference labels.

The medical work station shown in FIG. 4 differs essentially from the medical work station of FIG. 1 in that the robot R or its robot arm M does not guide the ultrasonic transducer 2, but rather the cannula K. The ultrasonic transducer 2, by contrast, is guided manually by the doctor. On the basis of the signals coming from the navigation system N, the position and possibly the orientation of the ultrasonic transducer 2 in space is detected, whereby the control device S is enabled to move the robot arm M in such a way that the cannula K automatically follows the manual motion of the ultrasonic transducer 2, in particular follows it constantly.

In the case of the present exemplary embodiment, it is provided that if the cannula K leaves the permitted area, i.e., the fat tissue of the person P, the motion of the robot R or its robot arm M is stopped by the control device S. Thus it can be ensured, at least to a large extent, that the cannula K or its tip is located exclusively within the fat tissue, whereby the danger of suctioning off healthy tissue is at least reduced.

The invention claimed is:

1. A medical work station, comprising:
   a medical instrument adapted to be inserted at least partially into the interior of a living being for treating the living being,
   an imaging device adapted to create image data records of the interior of the living being during the treatment, and
   a first robot, comprising:
      a first robot arm having a plurality of serially arranged links connected by joints, one of the imaging device or the medical instrument being attached to the first robot arm, and
      a first control device adapted to move the first robot arm in such a way that the imaging device follows a motion of the medical instrument, or the medical instrument follows a motion of the imaging device, and
   a second robot comprising a second robot arm having a plurality of serially arranged links connected by joints and comprising a second control device adapted for moving the second robot arm, wherein one of the first or second robot arms is adapted to move the imaging device and the other robot arm is adapted to move the medical instrument, and
   wherein one of the first or second robot arms is movable during the treatment by manually by pulling and/or pushing on the structure of that robot arm, and the other robot arm, controlled by its control device, automatically follows the motion of the manually moved robot arm.

2. The medical work station according to claim 1, wherein the imaging device is an ultrasonic transducer adapted to create ultrasound image records of the interior of the living being.

3. The medical work station according to claim 1, further comprising a navigation system connected to the first or second control device and adapted to ascertain the positions and/or locations of the first robot arm or second robot arm, the medical instrument and/or the imaging device, on the basis of which the control device connected with the navigation system moves the respective robot arm, so that the imaging device follows the motion of the medical instrument, or the medical instrument follows the motion of the imaging device.

4. The medical work station according to claim 1, further comprising a computer adapted to analyze the image data records and identify areas of the living being that are to be treated and areas of the living being that are not to be treated.

5. The medical work station according to claim 4, wherein the control device is adapted to stop or prevent a motion of at least one of the first robot arm or the second robot arm on the basis of an analyzed image data record, when the medical instrument is attached to one of the first or second robot arms and is located outside of the areas of the living being that are to be treated or threatens to leave the areas of the living being that are to be treated.

6. The medical work station according to claim 4, wherein the computer is configured to produce a warning signal on the basis of an analyzed image data record, if the medical instrument is located outside of the areas of the living being that are to be treated or threatens to leave the areas of the living being that are to be treated.

7. The medical work station according to claim 6, wherein the warning is an acoustic warning signal.

8. The medical work station according to claim 6, wherein the medical instrument has a vibration emitter and the warning is a vibration created by the vibration emitter.

9. The medical work station according to claim 1, further comprising a display device adapted to visually depict an image assigned to an image data record created by the imaging device.

10. The medical work station according to claim 9, further comprising a computer adapted to identify areas of the living being that are to be treated and areas of the living being that are not to be treated in the image depicted by the display device.

11. The medical work station according to claim 1, wherein the manually movable robot arm is provided with the medical instrument, and at least one of the first control device or the second control device of the medical work station is configured to prevent, or at least impede, a motion of the robot arm provided with the medical instrument if the medical instrument is located outside of the areas of the living being that are to be treated or threatens to leave areas of the living being that are to be treated.

12. The medical work station according to claim 1, wherein the medical instrument is a cannula adapted for suctioning off fat tissue of the living being.

* * * * *